United States Patent [19]

Aloup et al.

[11] 4,272,534
[45] Jun. 9, 1981

[54] 2-(PYRID-2-YL)TETRAHYDROTHIOPHENE DERIVATIVES

[75] Inventors: Jean-Claude Aloup, Villeneuve-le-Roi; Jean Bouchaudon, Morsang-sur-Orge; Daniel Farge, Thiais; Claude James, Paris, all of France

[73] Assignee: Rhone-Poulenc Industries, Paris, France

[21] Appl. No.: 134,311

[22] Filed: Mar. 26, 1980

[30] Foreign Application Priority Data

Mar. 30, 1979 [FR] France ............................... 79 08032
Jan. 24, 1980 [FR] France ............................... 80 01499
Jan. 24, 1980 [FR] France ............................... 80 01500

[51] Int. Cl.³ .................. A61K 31/44; A61K 31/495; C07D 413/14
[52] U.S. Cl. .............................. 424/248.51; 424/250; 424/263; 424/267; 544/131; 544/360; 546/193; 546/284
[58] Field of Search ................ 546/284, 193; 424/263, 424/267, 250, 248.51; 544/131, 360

[56] References Cited

U.S. PATENT DOCUMENTS

| | | | |
|---|---|---|---|
| 3,740,409 | 6/1973 | Brenner et al. | 546/284 |
| 3,873,536 | 3/1975 | Caldwell et al. | 546/284 |
| 3,898,228 | 8/1975 | Loev | 544/131 |
| 3,917,593 | 11/1975 | Loev | 546/193 |

FOREIGN PATENT DOCUMENTS

| | | | |
|---|---|---|---|
| 2100970 | 3/1972 | France | 546/284 |
| 2258178 | 1/1975 | France | 546/284 |

Primary Examiner—Alan L. Rotman
Attorney, Agent, or Firm—Stevens, Davis, Miller & Mosher

[57] ABSTRACT

Compounds of the formula:

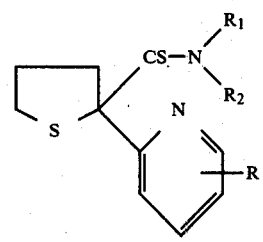

wherein R represents hydrogen or alkyl of 1 through 4 carbon atoms, and $R_1$ and $R_2$ represent hydrogen or alkyl of 1 through 15 carbon atoms, or alkyl of 1 through 15 carbon atoms substituted by one substituent selected from (i) hydroxy, (ii) alkylamino in which the alkyl radical is of 1 through 4 carbon atoms, (iii) dialkylamino in which the alkyl radicals are of 1 through 4 carbon atoms, (iv) phenyl, (v) carboxy, and (vi) alkoxycarbonyl in which the alkoxy radical is of 1 through 4 carbon atoms, or $R_1$ and $R_2$ together with the nitrogen atom to which they are attached represent a five- or six-membered heterocyclic radical, are new compounds. They possess pharmacological properties and are particularly useful in the treatment of gastro-intestinal ulcers.

11 Claims, No Drawings

2-(PYRID-2-YL)TETRAHYDROTHIOPHENE DERIVATIVES

DESCRIPTION

This invention relates to new 2-(pyrid-2-yl)-tetrahydrothiophene derivatives, to processes for their preparation and pharmaceutical compositions containing them.

The new 2-(pyrid-2-yl)tetrahydrothiophene derivatives of the present invention are those compounds of the general formula:

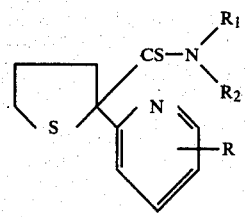

wherein R represents a hydrogen atom or an alkyl radical containing 1 to 4 carbon atoms, and $R_1$ and $R_2$, which have the same or different significances, represent a hydrogen atom or an alkyl radical containing 1 to 15 carbon atoms or such an alkyl radical substituted by (i) a hydroxy radical, (ii) an alkylamino group in which the alkyl radical contains 1 to 4 carbon atoms, (iii) a dialkylamino group in which the alkyl radicals each contain 1 to 4 carbon atoms, (iv) a phenyl radical, (v) a carboxy radical, or (vi) an alkoxycarbonyl group in which the alkoxy radical contains 1 to 4 carbon atoms, or $R_1$ and $R_2$ together with the nitrogen atom to which they are attached represent a five- or six-membered heterocyclic radical which may contain another heteroatom selected from oxygen, sulphur and nitrogen, which in the case of a nitrogen atom may optionally carry as substituent by an alkyl radical containing 1 to 4 carbon atoms, and—when appropriate—salts thereof. It is to be understood that the aforementioned alkyl and alkoxy radicals have straight- or branched-chains.

Examples of alkyl radicals represented by symbol $R_1$ and/or $R_2$ are methyl, ethyl, butyl, heptyl and dodecyl. Examples of groups represented by $R_1$ and/or $R_2$ when the symbol represents an alkyl radical substituted by (i) a hydroxy radical is 2-hydroxyethyl, (ii) an alkylamino group is 2-methylaminoethyl, (iii) a dialkylamino group is 2-dimethylaminoethyl, (iv) a phenyl group is benzyl, (v) a carboxy group is 2-carboxyethyl, or (vi) an alkoxycarbonyl group is 2-methoxycarbonyl-ethyl. Examples of heterocyclic radicals represented by the grouping —$NR_1R_2$ are piperidino, morpholino, and piperazin-1-yl optionally substituted on the 4-position nitrogen atom by an alkyl radical containing 1 to 4 carbon atoms (preferably methyl).

According to a feature of the present invention, the compounds of general formula I, wherein R, $R_1$ and $R_2$ are as hereinbefore defined, are prepared by the process which comprises reacting ammonia or an amine of the general formula:

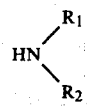

(wherein $R_1$ and $R_2$ are as hereinbefore defined) with a dithio-ester of the general formula:

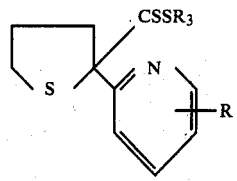

wherein R is as hereinbefore defined, and $R_3$ represents an alkyl radical containing 1 to 4 carbon atoms, or a benzyl or carboxymethyl radical.

Generally the reaction is carried out with an excess of the amine of general formula II either without a solvent or in an organic solvent, such as an aromatic hydrocarbon, an ether or a low molecular weight alcohol, or a mixture of such solvents, at a temperature between 20° and 130° C. and optionally under pressure.

When $R_1$ and/or $R_2$ represent(s) an alkyl radical containing 1 to 15 carbon atoms substituted by an alkylamino group, the amino radical in the alkylamino group(s) is advantageously protected beforehand by a labile protective group and then liberated after the reaction with the dithio-ester of general formula III. The blocking and the unblocking of the amine group can be carried out by any method known per se and which does not affect the rest of the molecule. Examples which may be mentioned are (a) blocking with a benzyl or benzyloxycarbonyl radical, followed by unblocking by hydrogenolysis in the presence of palladium-on-charcoal; or (b) blocking with a tert-butoxycarbonyl or trityl radical, followed by unblocking by acidolysis in an anhydrous medium.

The dithio-esters of general formula III can be obtained by reacting an organo-lithium compound with a 2-(pyrid-2-yl)tetrahydrothiophene of the general formula:

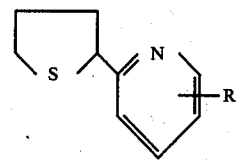

(wherein R is as hereinbefore defined), reacting the resulting mixture with carbon disulphide and then with a compound of the general formula:

$R_3$—Y         V wherein $R_3$ is as hereinbefore defined and Y represents a halogen atom or the residue of another reactive ester preferably a chlorine, bromine or iodine atom or a mesyloxy or tosyloxy radical. The reaction is generally carried out in an anhydrous organic solvent, such as hexamethylphosphorotriamide, to which an ether such as tetrahydrofuran has generally been added, at a temperature between −80° and −40° C.

Particularly suitable organo-lithium compounds are alkyllithium compounds, such as butyllithium and isopropyllithium, or phenyllithium, dissolved in an inert organic solvent such as hexane.

The 2-(pyrid-2-yl)tetrahydrothiophenes of general formula IV can be obtained in accordance with one of the following methods:

(1) The cyclisation by means of an organic base, such as an alkali metal alkoxide, of a pyridine derivative of the general formula:

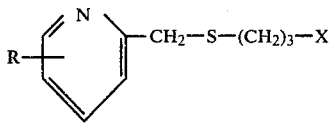　　　VI wherein R is as hereinbefore defined and X represents a halogen atom or another residue of reactive ester, preferably a chlorine or bromine atom or a mesyloxy or tosyloxy radical, the reaction being carried out in an anhydrous organic solvent, such as tetrahydrofuran, hexamethylphosphorotriamide or a mixture of these solvents, at a temperature of about 25° C. Potassium tert-butoxide is particularly advantageously used as the organic base.

The pyridine derivatives of general formula VI can be obtained by subjecting an acid addition salt of an isothiourea of the general formula:

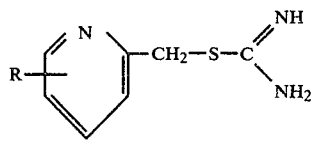　　　VII (wherein R is as hereinbefore defined) to alkaline hydrolysis, preferably by means of an aqueous solution of an alkali metal hydroxide such as sodium hydroxide, at a temperature between 50° C. and the boiling point of the reaction mixture, and subsequently reacting the resulting mixture with a compound of the general formula:

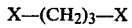X—(CH$_2$)$_3$—X　　　VIII (wherein the symbols X, which have the same or different significances, each represent a halogen atom or another residue of a reactive ester, preferably a chlorine or bromine atom or a mesyloxy or tosyloxy radical) at a temperature of about 20° C., in the presence of an alkali metal hydroxide such as sodium hydroxide.

It is possible to isolate, as an intermediate, the pyridine derivative of the general formula:

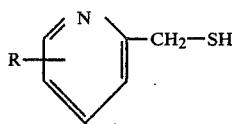　　　IX (wherein R is as hereinbefore defined), the said derivative originating from the alkaline hydrolysis of the isothiourea of general formula VII, and then to react this derivative with the compound of general formula VIII in the presence of an alkali metal hydroxide such as sodium hydroxide.

The isothiourea compounds of general formula VII, in the form of an acid addition salt such as the dihydrochloride, can be obtained by reacting thiourea with a pyridine derivative of the general formula:

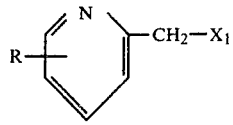　　　X (wherein R is as hereinbefore defined and X$_1$ represents a halogen atom, preferably a chlorine or bromine atom), optionally in the form of an acid addition salt such as a hydrohalide, the reaction being carried out in an organic solvent, such as an alcohol (e.g. ethanol), at the reflux temperature of the reaction mixture.

The pyridine derivatives of the general formula X can be prepared in accordance with the method of W. Mathes and H. Schüly, Angew. Chem. International Edition, 2, 144 (1963).

(2) The reaction of a compound of general formula VIII with a pyridine derivative of general formula IX. The reaction is generally carried out in an anhydrous organic solvent, such as tetrahydrofuran, in the presence of a sufficient amount of an organo-lithium derivative, such as an alkyllithium and/or a lithium dialkylamide, at a temperature between −80° C. and −40° C.

According to another feature of the present invention, the compounds of general formula I, wherein R$_2$ represents a hydrogen atom and R$_1$ represents an alkyl radical containing 1 to 15 carbon atoms which is unsubstituted or substituted by a hydroxy radical, an alkylamino or dialkylamino group in which the alkyl radical(s) contain 1 to 4 carbon atoms, a phenyl or carboxy radical, or an alkoxycarbonyl group in which the alkoxy radical contains 1 to 4 carbon atoms, are obtained by the process which comprises reacting an organolithium derivative with a 2-(pyrid-2-yl)tetrahydrothiophene of general formula IV (wherein R is as hereinbefore defined), and subsequently reacting the resulting mixture with an isothiocyanate of the general formula:

R$_{1'}$—N═C═S　　　XI wherein R$_{1'}$ represents an alkyl radical containing 1 to 15 carbon atoms which is unsubstituted or substituted by a hydroxy radical, an alkylamino or dialkylamino group in which the alkyl radical(s) contain 1 to 4 carbon atoms, a phenyl or carboxy radical, or an alkoxycarbonyl group in which the alkoxy radical contains 1 to 4 carbon atoms.

The reaction is generally carried out in an anhydrous organic solvent, such as hexamethylphosphorotriamide, to which an ether such as tetrahydrofuran has generally been added, at a temperature between −80° and −40° C.

When R$_{1'}$ in the isothiocyanate reactant represents an alkyl radical containing 1 to 15 carbon atoms substituted by an alkylamino group or a hydroxy radical, the amino moiety in the alkylamino group or the hydroxy radical must be protected beforehand and then liberated after the reaction with the tetrahydrothiophene of general formula IV. The blocking and the unblocking can be carried out by any method known per se and which does not affect the rest of the molecule. Examples which may be mentioned in the case of the amine moiety are (a) blocking with a benzyl or benzyloxycarbonyl radical, followed by unblocking by hydrogenolysis in the presence of palladium-on-charcoal; or (b) blocking with a tert-butoxycarbonyl or trityl radical, followed by unblocking by acidolysis in an anhydrous medium.

An example which may be mentioned in the case of the hydroxy radical is blocking with a tetrahydropyranyl or tert-butyl radical, followed by unblocking by acidolysis in an aqueous medium.

Particularly suitable organo-lithium derivatives are alkyllithium compounds, such as butyllithium and isopropyllithium, phenyllithium, or lithium dialkylamides such as lithium diethylamide and lithium diisopropylamide.

The 2-(pyrid-2-yl)tetrahydrothiophenes of general formula IV can be obtained in accordance with one of the methods described above.

The products of general formula I so obtained can be purified by known methods, such as crystallisation, chromatography or successive extractions in an acid medium and then in a basic medium.

The compounds of general formula I wherein at least one of the symbols $R_1$ and $R_2$ represents an alkyl radical substituted by (i) an alkylamino or dialkylamino group, can be converted by methods known per se into acid addition salts, or (ii) a carboxy radical, by methods known per se into metal salts or salts with a nitrogen-containing base. They can be converted (i) into acid addition salts by reaction with an acid in an organic solvent such as an alcohol, a ketone, an ether or a chlorinated hydrocarbon; or (ii) into metal salts and salts of nitrogen-containing bases by reaction with, for example, an alkali metal base or an alkaline earth metal base, ammonia or a nitrogen-containing base, in a suitable solvent such as an alcohol, a ketone, an ether or water. The salt formed precipitates, if necessary after concentration of its solution; it is separated off by filtration or decantation.

The new compounds of general formula I, and—when appropriate—their salts, possess particularly valuable pharmacological properties coupled with a low toxicity. They show a remarkable anti-ulcer and antisecretory activity which has been demonstrated on rats at doses of between 1 and 100 mg/kg animal body weight administered orally, in particular using the technique of Rossi et al., C.R. Soc. Biol., 150, 2124 (1956) and the technique of Shay et al., Gastroenterology, 5, 43 (1945).

Their toxic dose ($LD_{50}$), in mice, is generally more than 300 mg/kg animal body weight administered orally.

For therapeutic use, the compounds of general formula I can be employed as such or—when appropriate—in the form of a pharmaceutically acceptable salt, i.e. a salt which is non-toxic at the use doses.

Examples of pharmaceutically acceptable salts are—as appropriate—salts with alkali metals (such as the potassium, sodium or lithium salt) or with alkaline earth metals, ammonium salts, salts with nitrogen-containing bases (e.g. ethanolamine or lysine) and acid addition salts with inorganic acids (such as the hydrochlorides, sulphates, nitrates or phosphates) or with organic acids (such as the acetates, propionates, succinates, benzoates, fumarates, maleates, methanesulphonates, isethionates, theophylline-acetates, salicylates, phenolphthalinates or methylene-bis-$\beta$-oxynaphthoates).

Preferred compounds of general formula I are those wherein R is as hereinbefore defined, $R_1$ represents a hydrogen atom or an unsubstituted alkyl radical containing 1 to 4 carbon atoms, and $R_2$ represents a hydrogen atom, for example 2-(pyrid-2-yl)-tetrahydrothiophene-2-carbothioamide, 2-(6-methylpyrid-2-yl)tetrahydrothiophene-2-carbothioamide, N-methyl-2-(6-methylpyrid-2-yl)tetrahydrothiophene-2-carbothioamide, N-ethyl-2-(pyrid-2-yl)tetrahydrothiophene-2-carbothioamide, N-n-butyl-2-(pyrid-2-yl)tetrahydrothiophene-2-carbothioamide, N-methyl-2-(4-methylpyrid-2-yl)tetrahydrothiophene-2-carbothioamide, N-methyl-2-(5-methylpyrid-2-yl)tetrahydrothiophene-2-carbothioamide, and 2-(4-n-butylpyrid-2-yl)-2-methylaminocarbothioyltetrahydrothiophene.

Of outstanding interest are the compounds of general formula I wherein R is as hereinbefore defined, $R_1$ represents a methyl radical or a hydrogen atom, and $R_2$ represents a hydrogen atom, in particular N-methyl-2-(pyrid-2-yl)tetrahydrothiophene-2-carbothioamide.

The following non-limitative Examples illustrate the preparation of 2-(pyrid-2-yl)-tetrahydrothiophene derivatives of the present invention.

In the Examples chromatography—when referred to—was carried out with silica having a particle size of 0.063–0.20 mm or with alumina having a particle size of 0.125–0.15 mm.

EXAMPLE 1

A stream of anhydrous gaseous ammonia is introduced through a dip tube into a solution of methyl 2-(pyrid-2-yl)tetrahydrothiophene-2-carbodithioate (25.5 g) in a mixture of anhydrous diethyl ether and anhydrous ethanol (83:17 by volume; 360 cc) for 5 hours 45 minutes at a temperature of 25° C. The reaction mixture is subsequently stirred for 15 hours at the same temperature and ammonia gas is then introduced again for 7 hours. The crystals which have appeared are filtered off, washed with diethyl ether (25 cc) and dried under reduced pressure (20 mm Hg; 2.7 kPa) at a temperature of about 20° C. A first fraction of product (12 g) is thus obtained. The stirred filtrate is again saturated with ammonia gas for 1 hour 30 minutes at a temperature of about 24° C. The mixture is left to stand for 15 hours at a temperature of about 20° C. and then stirred again, ammonia gas being introduced for 6 hours at a temperature of about 24° C. The crystals which have appeared are filtered off, washed with diethyl ether (25 cc) and dried under reduced pressure (20 mm Hg; 2.7 kPa) at a temperature of about 20° C. The first fraction (12 g) is added to the resulting product (5 g), the whole is then dissolved in boiling acetonitrile (400 cc) and the solution, to which decolourising charcoal (0.3 g) is added, is filtered hot and then kept, after cooling, for 1 hour at a temperature of about 0° C. The crystals which have appeared are filtered off and dried under reduced pressure (20 mm Hg; 2.7 kPa) at a temperature of about 20° C. The resulting product (14.5 g) is dissolved in boiling acetonitrile (350 cc) and the solution is filtered hot and then kept, after cooling, for 1 hour at a temperature of about 0° C. The resulting crystals are filtered off, washed with acetonitrile (25 cc) and dried under reduced pressure (1 mm Hg; 0.13 kPa) at 60° C. 2-(Pyrid-2-yl)tetrahydrothiophene-2-carbothioamide (12.8 g), melting at 192° C., is thus obtained.

Methyl 2-(pyrid-2-yl)tetrahydrothiophene-2-carbodithioate can be prepared in the following manner:

A mixture of anhydrous hexamethylphosphorotriamide and anhydrous tetrahydrofuran (47:53 by volume; 320 cc) is added dropwise, in the course of 10 minutes, to a 1.6 M solution of n-butyllithium in hexane (432 cc), which is kept under an argon atmosphere and has been cooled to −65° C.

A solution of 2-(pyrid-2-yl)tetrahydrothiophene (66 g) in a mixture of anhydrous hexamethylphosphorotriamide and anhydrous tetrahydrofuran (47:53 by volume; 320 cc) is then added in the course of 18 minutes. After stirring for 15 minutes at −65° C., a solution of carbon disulphide (53 g) in a mixture of anhydrous hexamethylphosphorotriamide and anhydrous tetrahydrofuran (47:53 by volume; 300 cc) is added in the course of 15 minutes. After stirring for 5 minutes at −60° C., a solution of methyl iodide (98.6 g) in a mixture of anhydrous hexamethylphosphorotriamide and anhydrous tetrahydrofuran (47:53 by volume; 300 cc) is added in the course of 30 minutes at a temperature of about −60° C. The reaction mixture is subsequently stirred for 1 hour at the same temperature and then for 55 minutes whilst allowing the temperature to rise gradually to +15° C. After cooling distilled water (2000 cc), the reaction mixture is extracted twice with ethyl acetate (1800 cc in total). The combined organic extracts are washed three times with distilled water (6000 cc in total). After drying over anhydrous sodium sulphate, filtering and concentrating to dryness, a brown oil (145 g) is obtained. This oil (135 g) is chromatographed on neutral silica gel (1100 g) contained in a column of diameter 6.5 cm. Elution is carried out with methylene chloride (3500 cc), 500 cc fractions being collected. Fractions 6 and 7 are combined and evaporated to dryness. The resulting residue (38 g) is dissolved in boiling diisopropyl ether (150 cc) and the solution, to which decolourising charcoal (0.5 g) is added, is filtered hot and then kept, after cooling, for 1 hour at a temperature of about 0° C. The crystals which have appeared are filtered off, washed with diisopropyl ether (12 cc) and then twice with petroleum ether (24 cc in total) and dried under reduced pressure (20 mm Hg; 2.7 kPa) at a temperature of about 20° C. to give 30 g of product. 15 g thereof are dissolved in boiling diisopropyl ether (80 cc) and the solution, to which the decolourising charcoal (0.3 g) is added, is filtered hot and kept, after cooling, for 1 hour at a temperature of about 0° C. The resulting crystals are filtered off, washed with diisopropyl ether (10 cc) and then twice with petroleum ether (20 cc in total) and dried under reduced pressure (1 mm Hg; 0.13 kPa) at a temperature of about 20° C. Methyl 2-(pyrid-2-yl)tetrahydrothiophene-2-carbodithioate (12.4 g), melting at 64° C., is thus obtained.

2-(Pyrid-2-yl)tetrahydrothiophene can be prepared in accordance with one of the following processes:

(a) A solution of pyrid-2-ylmethyl 3-chloropropyl sulphide (330 g) in anhydrous tetrahydrofuran (400 cc) is added dropwise, in the course of 20 minutes, at a temperature of about 25° C., to a solution of potassium tert.-butylate (283 g) in a mixture of anhydrous hexamethylphosphorotriamide (428 cc) and anhydrous tetrahydrofuran (2300 cc). After stirring for 1 hour, the reaction mixture is added to a mixture of distilled water (4200 cc) and diethyl ether (2500 cc). After decantation, the aqueous phase is again extracted with diethyl ether (1700 cc). The combined ether extracts are washed three times with distilled water (12600 cc in total), dried over anhydrous sodium sulphate and concentrated to dryness. 2-(Pyrid-2-yl)-tetrahydrothiophene (189 g) is thus obtained in the form of a brown oil [Rf=0.56; chromatography on a thin layer of silica gel; solvent: ethyl acetate-cyclohexane (50:50 by volume)].

(b) A solution of diisopropylamine (152 g) in anhydrous tetrahydrofuran (500 cc) is added dropwise, in the course of 15 minutes, to a 1.6 M solution of n-butyllithium in hexane (940 cc), which has been cooled to −50° C. After stirring for 10 minutes and then cooling to −70° C., a mixture of pyrid-2-lymethanethiol (62.5 g) and 1-bromo-3-chloropropane (84 g), dissolved in anhydrous tetrahydrofuran (1000 cc), is added dropwise in the course of 25 minutes. The reaction mixture is subsequently stirred for 90 minutes at −70° C. and then for 30 minutes whilst allowing the temperature to rise from +70° C. to +5° C. After adding distilled water (2500 cc), the mixture is extracted twice with diethyl ether (2500 cc in total). The combined ether extracts are washed three times with distilled water (7500 cc in total), dried over anhydrous sodium sulphate and evaporated. A brown oil (75.5 g) is thus obtained. This oil (68 g) is chromatographed on neutral silica gel (350 g) contained in a column of diameter 4.6 cm. Elution is carried out successively with methylene chloride (10000 cc), a methylene chloride-ethyl acetate mixture (95:5 by volume; 2000 cc) and a methylene chloride-ethyl acetate mixture (90:10 by volume; 1000 cc), the following fractions of eluate being successively collected: 1000 cc (1), 330 cc (2), 670 cc (3) and eleven 1000 cc fractions (4 to 14). Fractions 3 to 14 are combined and concentrated to dryness. 2-(Pyrid-2-yl)tetrahydrothiophene (38 g) is thus obtained in the form of an oil.

Pyrid-2-ylmethanethiol can be prepared in accordance with the method described in U.S. Pat. No. 2,951,848.

Pyrid-2-ylmethyl 3-chloropropyl sulphide can be prepared in accordance with one of the following processes:

(a) Pyrid-2-ylmethanethiol (3.1 g) is added, in the course of 2 minutes, to a solution of potassium hydroxide pellets (85% pure; 2 g) in distilled water (10 cc), which is kept at a temperature of about 20° C. After stirring for 10 minutes, 1-bromo-3-chloropropane (3.95 g) is added in the course of 10 minutes. The reaction mixture is stirred for 16 hours at the same temperature and methylene chloride (50 cc) is then added. The organic phase is separated by decantation and then washed twice with distilled water (100 cc in total), dried over anhydrous sodium sulphate and concentrated to dryness. A red-brown liquid (4.3 g) is thus obtained and this is chromatographed on neutral silica gel (11 g) contained in a column of diameter 1.4 cm. Elution is carried out successively with cyclohexane (300 cc), a mixture of cyclohexane and ethyl acetate (99:1 by volume; 100 cc) and a cyclohexane-ethyl acetate mixture (98:2 by volume; 100 cc), 100 cc fractions being collected. Fractions 3 to 5 are combined and concentrated to dryness under reduced pressure (20 mm Hg; 2.7 kPa) at 40° C. A yellow liquid (2.7 g), containing an insoluble material, is thus obtained. After adding diethyl ether (25 cc), the insoluble material is filtered off. The filtrarte is concentrated under reduced pressure (20 mm Hg) at a temperature of about 20° C. Pyrid-2-ylmethyl 3-chloropropyl sulphide (2.3 g) is thus obtained in the form of a clear yellow liquid [Rf=0.51; chromatography on a thin layer of silica gel; solvent: ethyl acetate/cyclohexane (50:50 by volume)].

(b) A solution of sodium hydroxide pellets (151 g) in distilled water (342 cc) is added, in the course of 5 minutes, at a temperature which does not exceed 10° C., to a solution, originally at 5° C., of 2-(pyrid-2-ylmethyl)-isothiourea dihydrochloride (453 g) in distilled water (840 cc). After heating the reaction mixture for 20 minutes at a temperature of about 70° C., and then cooling to 3° C., a solution of sodium hydroxide pellets (92.5 g)

in distilled water (210 cc) is added dropwise in the course of 3 minutes. After stirring the reaction mixture for 5 minutes at 10° C., 1-bromo-3-chloropropane (303 g) is added. Stirring is then continued for 20 hours at a temperature of about 20° C. The reaction mixture is then extracted four times with methylene chloride (1100 cc in total). The combined organic extracts are washed three times with distilled water (600 cc in total) and then dried over anhydrous sodium sulphate. After filtering, the resulting solution is poured onto neutral silica gel (380 g) contained in a column of diameter 6 cm, and the column is then washed with methylene chloride (2700 cc). A first fraction of effluent (600 cc) is discarded and a second fraction (3200 cc) is then collected and concentrated to dryness under reduced pressure (20 mm Hg) at 20° C. Pyrid-2-ylmethyl 3-chloropropyl sulphide (330 g) is thus obtained in the form of a yellow liquid.

2-(Pyrid-2-ylmethyl)isothiourea dihydrochloride can be prepared in the following manner:

A solution of 2-chloromethylpyridine hydrochloride (30 g) in ethanol (100 cc) at 60° C. is added dropwise, in the course of 15 minutes, to a suspension of thiourea (17.6 g) in boiling ethanol (100 cc). Boiling is maintained for 90 minutes and then, after cooling, the crystals which have appeared are filtered off, washed twice with ethanol (100 cc in total) and dried under reduced pressure (20 mm Hg) at a temperature of about 20° C., in the presence of potassium hydroxide pellets. 2-(Pyrid-2-ylmethyl)isothiourea dihydrochloride (41.7 g), melting at 220° C., is thus obtained.

2-Chloromethylpyridine hydrochloride can be prepared in accordance with the method described in German Patent No. 1,204,231.

EXAMPLE 2

By following the procedure of Example 1 but using methyl 2-(6-methylpyrid-2-yl)tetrahydrothiophene-2-carbodithioate (13.5 g) as the starting material, a first and a second fraction (5.8 g and 1.8 g respectively) of crystalline product are obtained after filtration, and a residue (5.1 g) is also obtained by concentrating the filtrate to dryness. The two fractions (7.6 g in total) are combined and dissolved in boiling ethanol (140 cc). The solution, to which decolourising charcoal is added, is filtered hot and then kept, after cooling, for 1 hour at a temperature of about 0° C. The crystals which have appeared are filtered off, washed twice with ethanol (10 cc in total) and dried under reduced pressure (20 mm Hg; 2.7 kPa) at a temperature of about 20° C. A crystalline product (5.9 g) is thus obtained. The residue (5.1 g) is dissolved in boiling ethanol (100 cc) and the solution, to which decolourising charcoal is added, is filtered hot and then kept, after cooling, for 1 hour at a temperature of about 0° C. The crystals which have appeared are filtered off, washed twice with ethanol (10 cc in total) and dried under reduced pressure (20 mm Hg; 2.7 kPa) at a temperature of about 20° C. 2.8 g of crystalline product are thus obtained and the 5.9 g obtained previously are added thereto. The mixture is dissolved in boiling ethanol (150 cc) and the solution, to which decolourising charcoal is added, is filtered hot and then kept, after cooling, for 1 hour at a temperature of about 20° C. The crystals which have appeared are filtered off, washed twice with ethanol (20 cc in total) and dried under reduced pressure (1 mm Hg; 0.13 kPa) at 50° C. 2-(6-Methylpyrid-2-yl)tetrahydrothiophene-2-carbothioamide (7.4 g), melting at 171° C., is thus obtained.

Methyl 2-(6-methylpyrid-2-yl)tetrahydrothiophene-2-carbodithioate can be prepared in the following manner:

By following the procedure described in Example 1 for the preparation of methyl 2-(pyrid-2-yl)tetrahydrothiophene-2-carbodithioate but using 2-(6-methylpyrid-2-yl)tetrahydrothiophene (32.8 g) and a 1.6 M solution of n-butyllithium in hexane (171 cc) as the starting materials, a crude product (73.4 g) is obtained and this is chromatographed on neutral silica gel (700 g) contained in a column of diameter 5.6 cm. Elution is carried out with a cyclohexane-ethyl acetate mixture (95:5 by volume; 3300 cc), one 1500 cc fraction and six 300 cc fractions being collected. Fractions 3 to 7 are combined and concentrated to dryness under reduced pressure (20 mm Hg; 2.7 kPa) at 40° C., and the residue (39.3 g) is dissolved in diisopropyl ether (200 cc). After cooling, the solution is kept for 1 hour at a temperature of about 0° C. The crystals which have appeared are filtered off, washed twice with diisopropyl ether (50 cc in total) and dried under reduced pressure (1 mm Hg; 0.13 kPa) at 50° C. Methyl 2-(6-methylpyrid-2-yl)tetrahydrothiophene-2-carbodithioate (30.3 g), melting at 80° C., is thus obtained.

2-(6-Methylpyrid-2-yl)tetrahydrothiophene can be prepared in the following manner:

A solution of diisopropylamine (113 g) in anhydrous tetrahydrofuran (380 cc) is added dropwise, in the course of 20 minutes, to a 1.6 M solution of n-butyllithium in hexane (663 cc), which has been cooled to −60° C. After stirring for 5 minutes, a mixture of 6-methylpyrid-2-ylmethanethiol (55.4 g) and 1-bromo-3-chloropropane (58 g), dissolved in anhydrous tetrahydrofuran (760 cc), is added dropwise in the course of 16 minutes, at the same temperature. The reaction mixture is subsequently stirred for 90 minutes at −70° C. and then for 90 minutes whilst allowing the temperature to rise from −70° C. to about 20° C.

After adding distilled water (1300 cc), the mixture is extracted three times with ethyl acetate (2600 cc in total). The combined organic extracts are washed three times with distilled water (1500 cc in total), dried over anhydrous sodium sulphate and concentrated to dryness. The residue (66.3 g) is chromatographed on neutral silica gel (330 g) contained in a column of diameter 4.5 cm. Elution is carried out with cyclohexane (4500 cc), a mixture of cyclohexane and ethyl acetate (98:2 by volume; 2000 cc) and a mixture of cyclohexane and ethyl acetate (90:10 by volume, 2000 cc), 500 cc fractions being collected. Fractions 5 to 17 are combined and evaporated to dryness under reduced pressure (20 mm Hg; 2.7 kPa) at 40° C. 2-(6-Methylpyrid-2-yl)tetrahydrothiophene (33.3 g) is thus obtained in the form of a yellow oil [Rf=0.65; chromatography on a thin layer of silica gel; solvent: ethyl acetate-cyclohexane (50:50 by volume)].

6-Methylpyrid-2-ylmethanethiol can be prepared in the following manner:

A solution of sodium hydroxide pellets (37 g) in distilled water (140 cc) is added dropwise, in the course of 15 minutes, to a solution, cooled to 15° C., of 2-(6-methylpyrid-2-ylmethyl)isothiourea dihydrochloride (114.7 g) in distilled water (280 cc). The reaction mixture is heated to the boil and is then stirred for 35 minutes. After cooling to 20° C., the reaction mixture is extracted three times with diethyl ether (480 cc in total). The combined ether extracts are washed three times with distilled water (300 cc in total), dried over anhydrous sodium sulphate and concentrated under reduced pressure (20 mm Hg) at 30° C. 6-Methylpyrid-2-ylmethanethiol (55.4 g) is thus obtained in the form of a yellow oil.

2-(6-Methylpyrid-2-ylmethyl)isothiourea dihydrochloride can be prepared in the following manner:

2-Chloromethyl-6-methylpyridine hydrochloride (89 g) is dissolved at 60° C. in ethanol (300 cc), and the resulting solution is added dropwise, in the course of 5 minutes, to a suspension of thiourea (47.5 g) in boiling ethanol (300 cc). Boiling is maintained for 90 minutes and then, after cooling to 5° C., the crystals which have appeared are filtered off and washed twice with ethanol (100 cc in total) and then with diisopropyl ether (200 cc). After boiling under reduced pressure (20 mm Hg) at a temperature of about 20° C., in the presence of potassium hydroxide pellets, 2-(6-methylpyrid-2-ylmethyl)isothiourea dihydrochloride (111.7 g), melting at 222° C., is obtained.

2-Chloromethyl-6-methylpyridine hydrochloride can be prepared in accordance with the method described in German Patent 1204231.

EXAMPLE 3

A 33% (weight/volume) solution of methylamine in ethanol (7.5 cc) is added dropwise to a solution of methyl 2-(pyrid-2-yl)tetrahydrothiophene-2-carbodithioate (10 g) in ethanol (25 cc), which is kept at a temperature of about 20° C. The solution is kept for 30 minutes at a temperature of about 20° C. Crystals appear on cooling for 30 minutes at a temperature of about 0° C. They are filtered off, washed twice with ethanol (20 cc in total) and dried under reduced pressure (20 mm Hg; 2.7 kPa) at 20° C.

The product thus obtained (8.7 g) is dissolved in boiling ethanol (55 cc) and the solution, to which decolourising charcoal (0.2 g) is added, is filtered hot and then kept, after cooling, for 30 minutes at a temperature of about 0° C. The crystals which have appeared are filtered off, washed twice with ethanol (20 cc in total) and dried under reduced pressure (20 mm Hg; 2.7 kPa). N-Methyl-2-(pyrid-2-yl)-tetrahydrothiophene-2-carbothioamide (7.4 g), melting at 131° C., is thus obtained.

EXAMPLE 4

A solution of methyl 2-(pyrid-2-yl)tetrahydrothiophene-2-carbodithioate (6.4 g) and n-heptylamine (2.9 g) in ethanol (75 cc) is heated under reflux for 2 hours 30 minutes. The reaction mixture is concentrated to dryness (20 mm Hg; 2.7 kPa) at 40° C. 6.8 g of a product prepared under the same conditions are added to the resulting residue (8.2 g) and the whole is chromatographed on neutral silica gel (150 g) contained in a column of diameter 3.5 cm. Elution is carried out with a cyclohexane-ethyl acetate mixture (98:2 by volume; 7300 cc), the following fractions of eluate being collected: fraction 1: 600 cc, fractions 2 to 8: 250 cc each and fractions 9 to 47: 100 cc each. Fractions 14 to 40 are combined and concentrated to dryness under reduced pressure (2 mm Hg; 0.27 kPa) at a temperature of 40° C. N-n-Heptyl-2-(pyrid-2-yl)tetrahydrothiophene-2-carbothioamide (8.3 g) is thus obtained in the form of a clear yellow liquid [Rf=0.40; chromatography on a thin layer of silica gel; solvent: cyclohexane-ethyl acetate (80:20 by volume)].

EXAMPLE 5

A solution of methyl 2-(pyrid-2-yl)tetrahydrothiophene-2-carbodithioate (10 g) in n-dodecylamine (15 g) is heated for 50 minutes at 110° C. The reaction mixture is chromatographed on silica gel (200 g) contained in a column of diameter 3.7 cm. Elution is carried out with a cyclohexane-ethyl acetate mixture (90:10 by volume; 1800 cc), one 300 cc fraction and three 500 cc fractions being collected. Fractions 2 to 4 are combined and concentrated to dryness (20 mm Hg; 2.7 kPa) at 40° C.; the residue (14.2 g) is dissolved in ethanol (75 cc). The solution, to which decolourising charcoal (0.3 g) is added, is filtered hot and then kept, after cooling, for 30 minutes at a temperature of about 0° C. The crystals which have appeared are filtered off, washed twice with ethanol (40 cc in total) and dried under reduced pressure (20 mm Hg; 2.7 kPa) at a temperature of about 20° C. The resulting product (11.5 g) is dissolved in boiling ethanol (75 cc) and the solution, to which decolourising charcoal (0.3 g) is added, is filtered hot and then kept, after cooling, for 30 minutes at a temperature of about 0° C. The crystals which have appeared are filtered off, washed twice with ethanol (50 cc in total) and dried under reduced pressure (1 mm Hg; 0.13 kPa) at 35° C. N-n-Dodecyl-2-(pyrid-2-yl)tetrahydrothiophene-2-carbothioamide (10.2 g), melting at 60° C., is thus obtained.

EXAMPLE 6

A solution of methyl 2-(pyrid-2-yl)-tetrahydrothiophene-2-carbodithioate (10 g) in benzylamine (100 cc) is heated for 45 minutes at 110° C. After concentrating the reaction mixture to dryness, a residue (17.2 g) is obtained and this is chromatographed on silica gel (150 g) contained in a column of diameter 3.7 cm. Elution is carried out with a cyclohexaneethyl acetate mixture (90:10 by volume; 1500 cc), 250 cc fractions being collected. Fractions 3 to 6 are combined and concentrated to dryness (20 mm Hg; 2.7 kPa) at 40° C. The residue (10.5 g) is dissolved in boiling ethanol (50 cc) and the solution, to which decolourising charcoal (0.2 g) is added, is filtered hot and then kept, after cooling, for 15 hours at a temperature of about 5° C. The crystals which have appeared are filtered off, washed twice with ethanol (20 cc in total) and dried under reduced pressure (1 mm Hg; 0.13 kPa) at a temperature of about 40° C. N-Benzyl-2-(pyrid-2-yl)-tetrahydrothiophene-2-carbothioamide (8.1 g), melting at 71° C., is thus obtained.

EXAMPLE 7

A solution of methyl 2-(pyrid-2-yl)tetrahydrothiophene-2-carbodithioate (12.8 g) and ethanolamine (3 g) in ethanol (150 cc) is heated under reflux for 1 hour 30 minutes. After concentrating the reaction mixture to dryness (20 mm Hg; 2.7 kPa) at 50° C., the resulting residue (14.8 g) is dissolved in boiling ethanol (80 cc) and the solution, to which decolourising charcoal (0.3 g) is added, is filtered hot and then kept, after cooling, for 1 hour at a temperature of about 0° C. The crystals which have appeared are filtered off, washed twice with ethanol (30 cc in total) and dried under reduced pressure (1 mm Hg; 0.13 kPa) at 50° C. N-(2-Hydroxyethyl)-2-(pyrid-2-yl)tetrahydrothiophene-2-carbothioamide (11.4 g), melting at 132° C., is thus obtained.

EXAMPLE 8

A solution of methyl 2-(pyrid-2-yl)tetrahydrothiophene-2-carbodithioate (15 g) in N,N-dimethylethylenediamine (20.7 g) is heated for 55 minutes at a temperature of about 105° C. After concentrating the reaction mixture to dryness (2 mm Hg; 0.27 kPa) at 60° C., the resulting residue (18.4 g) is dissolved in ethanol (70 cc) and the solution, to which methanesulphonic acid (4 cc) is added, is concentrated to dryness (20 mm Hg; 2.7 kPa) at 50° C. The residue is dissolved in distilled water (250 cc) and the solution, which is rendered alkaline to pH 8 by adding a 2 M aqueous solution of sodium hydroxide (35 cc), is extracted three times with diethyl ether (450 cc in total). The combined organic extracts are washed twice with distilled water (100 cc in total) and dried over anhydrous sodium sulphate. Decolourising charcoal (0.5 g) is added thereto and the extracts are filtered and concentrated to dryness (20 mm Hg; 2.7 kPa) at 40° C. The residue (16 g) is chromatographed on alumina (160 g) contained in a column of diameter 2.7 cm. Elution is carried out with a cyclohexaneethyl acetate mixture (90:10 by volume; 1500 cc), one 500 cc fraction and ten 100 cc fractions being collected. Fractions 2 to 11 are combined and concentrated to dryness (20 mm Hg; 2.7 kPa) at 40° C. The residue (11.6 g) is dissolved in ethanol (200 cc) and the solution, to which methanesulphonic acid (3.8 g) is added, is kept for 2 hours at a temperature of about 20° C. The crystals which have appeared are filtered off, washed twice with ethanol (40 cc in total) and dried under reduced pressure (1 mm Hg; 0.13 kPa) at 55° C. N-(2-N,N-dimethylaminoethyl)-2-(pyrid-2-yl)tetrahydrothiophene-2-carbothioamide methanesulphonate (7.2 g), melting at 138° C., is thus obtained.

EXAMPLE 9

A solution of methyl 2-(pyrid-2-yl)tetrahydrothiophene-2-carbodithioate (20 g) in dimethylamine (100 cc) is heated gradually for 3 hours 40 minutes, in an autoclave, up to a temperature of about 125° C. After cooling to a temperature of about 20° C., the autoclave is emptied and rinsed with methylene chloride (200 cc), the latter being added to the reaction mixture. The solution is concentrated to dryness (20 mm Hg; 2.7 kPa) at 40° C. The resulting residue (20.7 g) is dissolved in boiling ethanol (50 cc) and the solution, to which decolourising charcoal (0.5 g) is added, is filtered hot and then kept, after cooling, for 1 hour at a temperature of about 0° C. The crystals which have appeared are filtered off, washed twice with ethanol (20 cc in total) and dried under reduced pressure (20 mm Hg; 2.7 kPa) at a temperature of about 20° C. The resulting product (14.1 g) is dissolved in boiling ethanol (45 cc) and the solution, to which decolourising charcoal (0.5 g) is added, is filtered hot and then kept, after cooling, for 1 hour at a temperature of 0° C. The crystals which have appeared are filtered off, washed twice with ethanol (20 cc in total) and dried under reduced pressure (1 mm Hg; 0.13 kPa) at 45° C. N,N-Dimethyl-2-(pyrid-2-yl)-tetrahydrothiophene-2-carbothioamide (11.8 g), melting at 100° C., is thus obtained.

EXAMPLE 10

A solution of methyl 2-(pyrid-2-yl)tetrahydrothiophene-2-carbodithioate (19 g) in morpholine (280 cc) is kept under reflux for 2 hours. After concentrating the reaction mixture to dryness (2 mm Hg; 0.27 kPa) at 90° C., a residue (23 g) is obtained. This is dissolved in boiling ethanol (200 cc) and the solution, to which decolourising charcoal (0.2 g) is added, is filtered hot and then kept, after cooling, for 1 hour at a temperature of about 0° C. The crystals which have appeared are filtered off, washed with ethanol (20 cc) and dried under reduced pressure (20 mm Hg; 2.7 kPa) at a temperature of about 20° C. The product thus obtained (16.5 g) is dissolved in boiling ethanol (145 cc) and the solution, to which decolourising charcoal (0.2 g) is added, is filtered hot and then kept, after cooling, for 1 hour 30 minutes at a temperature of about 0° C. The resulting crystals are filtered off and washed with ethanol (15 cc) and then with diisopropyl ether (15 cc). After drying under reduced pressure (1 mm Hg; 0.13 kPa) at 55° C., 2-morpholinocarbothioyl-2-(pyrid-2-yl)tetrahydrothiophene (12.5 g) melting at 139° C., is obtained.

EXAMPLE 11

A solution of methyl 2-(pyrid-2-yl)tetrahydrothiophene-2-carbodithioate (20 g) in piperidine (100 cc) is heated for 1 hour at a temperature of about 100° C. After concentrating the reaction mixture to dryness (2 mm Hg; 0.27 kPa) at 60° C., a brown oil (26.1 g) is obtained and this is chromatographed on neutral silica gel (260 g) contained in a column of diameter 4 cm. Elution is carried out successively with cyclohexane (1250 cc), a cyclohexane-ethyl acetate mixture (99:1 by volume; 1250 cc), a cyclohexaneethyl acetate mixture (98:2 by volume; 1250 cc), a cyclohexane-ethyl acetate mixture (97:3 by volume; 3250 cc) and a cyclohexaneethyl acetate mixture (95:5 by volume; 4250 cc), 250 cc fractions being collected. Fractions 29 to 46 are combined and concentrated to dryness (20 mm Hg; 2.7 kPa) at 40° C. The resulting product (10.5 g) is dissolved in boiling isopropanol (55 cc) and the solution, to which decolourising charcoal (0.2 g) is added, is filtered hot and then kept, after cooling, for 1 hour at a temperature of about 0° C. The crystals which have appeared are filtered off, washed twice with isopropanol (20 cc in total) and dried under reduced pressure (1 mm Hg; 0.13 kPa) at 50° C. 2-Piperidinocarbothioyl-2-(pyrid-2-yl)-tetrahydrothiophene (5.4 g), melting at 90° C., is thus obtained.

EXAMPLE 12

A solution of methyl 2-(pyrid-2-yl)tetrahydrothiophene-2-carbodithioate (20 g) in N-methylpiperazine (35 cc) is heated for 1 hour 15 minutes at 110° C. After concentrating the reaction mixture to dryness (2 mm Hg; 0.27 kPa) at 70° C., a residue (26.7 g) is obtained and this is chromatographed on alumina (270 g) contained in a column of diameter 3.4 cm. Elution is carried out with a cyclohexane-ethyl acetate mixture (80:20 by volume; 1900 cc), 100 cc fractions being collected. Fractions 5 to 14 are combined and concentrated to dryness (20 mm Hg; 2.7 kPa) at 40° C. The residue (20.4 g) is dissolved in boiling ethanol (45 cc) and the solution, to which decolourising charcoal (0.4 g) is added, is filtered hot and then kept, after cooling, for 1 hour at a temperature of the order of 0° C. The crystals which have appeared are filtered off, washed twice with diisopropyl ether (20 cc) and dried under reduced pressure (20 mm Hg; 2.7 kPa) at a temperature of about 20° C. A crystalline product (5.4 g) is thus obtained and, after concentrating the filtrate to dryness (20 mm Hg; 2.7 kPa) at 40° C., a residue (13.5 g) is obtained. The latter is chromatographed on alumina (135 g) contained in a column of diameter 2.7 cm. Elution is carried out successively with cyclohexane (1000 cc), a cyclohexane-ethyl acetate mixture (99:1 by volume; 200 cc), a cyclohexaneethyl acetate mixture (98:2 by volume; 1800 cc) and a cyclohexane-ethyl acetate mixture (96:4 by volume;

2000 cc), 100 cc fractions being collected. Fractions 13 to 50 are combined and concentrated to dryness (20 mm Hg; 2.7 kPa) at 40° C.; the resulting residue (6.2 g) is dissolved in boiling diisopropyl ether (40 cc) and the solution, after cooling, is kept for 1 hour at a temperature of about 0° C. The crystals which have appeared are filtered off, washed twice with diisopropyl ether (4 cc in total) and dried under reduced pressure (20 mm Hg; 2.7 kPa) at a temperature of about 20° C. The fraction (5.4 g) isolated previously is added to the resulting product (1.9 g), the whole is then dissolved in boiling ethanol (35 cc) and the solution, to which decolourising charcoal (0.2 g) is added, is filtered hot and then kept, after cooling, for 1 hour at a temperature of about 0° C. The resulting crystals are filtered off, washed twice with ethanol (10 cc in total) and dried under reduced pressure (1 mm Hg; 0.13 kPa) at 40° C. 2-[(4-Methylpiperazin-1-yl)carbothioyl]-2-(pyrid-2-yl)-tetrahydrothiophene (5.3 g), melting at 124° C., is thus obtained.

EXAMPLE 13

A solution of diisopropylamine (22.5 g) in a mixture of anhydrous hexamethylphosphorotriamide and anhydrous tetrahydrofuran (47:53 by volume; 182 cc) is added dropwise, in the course of 14 minutes, to a 1.6 M solution of n-butyllithium in hexane (142 cc), which has been cooled to −55° C. The mixture is stirred for 5 minutes at a temperature of about −60° C. and a solution of 2-(pyrid-2-yl)tetrahydrothiophene (30 g) in a mixture of anhydrous hexamethylphosphorotriamide and anhydrous tetrahydrofuran (47:53 by volume; 182 cc) is added in the course of 13 minutes. After stirring for 7 minutes at −65° C., a solution of methyl isothiocyanate (16.8 g) in a mixture of anhydrous hexamethylphosphorotriamide and anhydrous tetrahydrofuran (47:53 by volume; 90 cc) is added in the course of 13 minutes at a temperature of the order of −60° C. The reaction mixture is subsequently stirred for 1 hour at the same temperature and then for 1 hour whilst allowing the temperature to rise gradually to +5° C. After adding distilled water (900 cc), the reaction mixture is extracted twice with ethyl acetate (900 cc in total). The combined organic extracts are washed three times with distilled water (2700 cc in total), dried over anhydrous sodium sulphate and concentrated to dryness. The residue (43 g) is dissolved in boiling ethanol (180 cc). After filtering hot, the solution is kept for 24 hours at a temperature of about 4° C. The crystals which have appeared are filtered off, washed with ethanol (10 cc) and then twice with diisopropyl ether (30 cc in total) and dried under reduced pressure (20 mm Hg) at a temperature of about 20° C., in the presence of potassium hydroxide pellets. 1.9 g of a product prepared under the same conditions are added to the product thus obtained (12.5 g), the whole is then dissolved in boiling ethanol (95 cc) and the solution, to which decolourising charcoal (1 g) is added, is filtered hot and then kept, after cooling, for 1 hour at a temperature of about 5° C. The crystals which have appeared are filtered off and washed with ethanol (10 cc) and then twice with diisopropyl ether (30 cc in total). After drying under reduced pressure (1 mm Hg) at 55° C., N-methyl-2-(pyrid-2-yl)tetrahydrothiophene-2-carbothioamide (12.5 g) melting at 131° C., is obtained.

EXAMPLE 14

Lithium (1.75 g) is added to a mixture of anhydrous toluene (62.5 cc) and anhydrous hexamethylphosphorotriamide (50 cc), which is kept under a nitrogen atmosphere, and a solution of diethylamine (18.2 g) in anhydrous hexamethylphosphorotriamide (12.5 cc) is then added dropwise to the resulting mixture, whilst keeping the temperature at 22° C. The mixture is stirred for 16 hours at a temperature of about 20° C.; a deep red solution (146 cc) is thus obtained. 14.6 cc of this solution are cooled to −55° C. A solution of 2-(pyrid-2-yl)tetrahydrothiophene (3.3 g) in a mixture of anhydrous hexamethylphosphorotriamide and anhydrous tetrahydrofuran (47:53 by volume; 20 cc) is added dropwise thereto in the course of 10 minutes. The reaction mixture is stirred for 10 minutes and a solution of methyl isothiocyanate (3.3 g) in the same mixture of hexamethylphosphorotriamide and tetrahydrofuran (10 cc) is then added dropwise, in the course of 10 minutes, at −60° C. After stirring for 1 hour at −60° C. and then for 1 hour whilst allowing the temperature to rise gradually to +5° C., distilled water (100 cc) is added cautiously to the reaction mixture and extraction is then carried out twice with ethyl acetate (100 cc in total). The combined organic extracts are washed three times with distilled water (300 cc in total), dried over anhydrous sodium sulphate and concentrated to dryness. The residue (6 g) is dissolved in boiling ethanol (25 cc) and the resulting solution is kept for 16 hours at a temperature of about 5° C. The crystals which have appeared are filtered off and washed with ethanol (2.5 cc) and then twice with diisopropyl ether (10 cc in total). After drying under reduced pressure (20 mm Hg) at a temperature of about 20° C., in the presence of potassium hydroxide pellets, N-methyl-2-(pyrid-2-yl)tetrahydrothiophene-2-carbothioamide (2.1 g), melting at 131° C., is obtained.

EXAMPLE 15

A solution of diisopropylamine (23.5 g) in a mixture of anhydrous hexamethylphosphorotriamide and anhydrous tetrahydrofuran (47:53 by volume; 135 cc) is added dropwise, in the course of 15 minutes, to a 1.6 M solution of n-butyllithium in hexane (145 cc), which has been cooled to −60° C. The mixture is stirred for 5 minutes at a temperature of about −60° C. and a solution of 2-(6-methylpyrid-2-yl)tetrahydrothiophene (33.3 g) in a mixture of anhydrous hexamethylphosphorotriamide and anhydrous tetrahydrofuran (47:53 by volume; 135 cc) is then added in the course of 15 minutes. After stirring for 15 minutes at a temperature of about −65° C., a solution of methyl isothiocyanate (20.2 g) in a mixture of anhydrous hexamethylphosphorotriamide and anhydrous tetrahydrofuran (47:53 by volume; 135 cc) is added in the course of 30 minutes at the same temperature. The reaction mixture is subsequently stirred for 45 minutes at −78° C. and then for 1 hour whilst allowing the temperature to rise gradually to 0° C. The reaction mixture is poured into distilled water (650 cc) and extraction is then carried out twice with ethyl acetate (650 cc in total). The combined organic extracts are washed three times with distilled water (600 cc in total), dried over anhydrous sodium sulphate and concentrated to dryness. The residue (42.5 g) is chromatographed on neutral silica gel (425 g) contained in a column of diameter 5 cm. Elution is carried out successively with cyclohexane (1000 cc), a mixture of cyclohexane and ethyl acetate (98:2 by volume; 1000 cc), a mixture of cyclohexane and ethyl acetate (96:4 by volume; 1000 cc), a mixture of cyclohexane and ethyl acetate (94:6 by volume; 4000 cc) and a mixture of cyclohexane and ethyl acetate (90:10 by volume; 6000 cc), 1000 cc fractions being collected.

Fractions 10 to 12 are combined and concentrated to dryness; a crude product (17.6 g) is thus obtained. Fractions 9 and 13 are also combined and evaporated, and the resulting residue, which is washed twice with diethyl ether (20 cc in total) and dried under reduced pressure (20 mm Hg) at a temperature of about 20° C., makes it possible to recover 2.3 g of product, and this is added to the 17.6 g obtained previously. The mixture is dissolved in methylene chloride (70 cc). Diethyl ether (350 cc) is added and the mixture is then kept for 1 hour at a temperature of about 5° C. The crystals which have appeared are filtered off, washed with diethyl ether (10 cc) and dried under reduced pressure (20 mm Hg) at a temperature of about 20° C.; a purified product (11.2 g) is thus obtained. The filtrate is concentrated to dryness under reduced pressure (20 mm Hg; 2.7 kPa) at 40° C., and the residue is dissolved in methylene chloride (20 cc) at 40° C. After adding diethyl ether (120 cc) to this solution and then cooling for 16 hours at a temperature of about 5° C., the crystals which have appeared are filtered off, washed with diethyl ether (10 cc) and dried under reduced pressure (20 mm Hg) at a temperature of about 20° C.; 3.7 g of product are thus obtained and this is added to the 11.2 g isolated previously. The mixture is dissolved in a boiling mixture of 1,2-dichloroethane and diethyl ether (12:88 by volume; 70 cc) and the filtered solution is kept for 1 hour at a temperature of the order of 5° C. The crystals which have appeared are filtered off and washed with a mixture of 1,2-dichloroethane and diethyl ether (12:88 by volume; 15 cc) and twice with diisopropyl ether (30 cc in total). After drying under reduced pressure (1 mm Hg) at 60° C., N-methyl-2-(6-methylpyrid-2-yl)tetrahydrothiophene-2-carbothioamide (12 g), melting at 121° C. is obtained.

EXAMPLE 16

A solution of diisopropylamine (33.7 g) in a mixture of anhydrous hexamethylphosphorotriamide and anhydrous tetrahydrofuran (47:53 by volume; 270 cc) is added dropwise, in the course of 15 minutes, to a 1.6 M solution of n-butyllithium in hexane (213 cc), which is kept under an argon atmosphere and has been cooled to −50° C. A solution of 2-(pyrid-2-yl)-tetrahydrothiophene (45 g) in a mixture of anhydrous hexamethylphosphorotriamide and anhydrous tetrahydrofuran (47:53 by volume; 270 cc) is then added in the course of 24 minutes at a temperature between −50° C. and −55° C. After stirring for 15 minutes at the same temperature, a solution of ethyl isothiocyanate (59.1 g) in a mixture of anhydrous hexamethylphosphorotriamide and anhydrous tetrahydrofuran (47:53 by volume; 270 cc) is added in the course of 25 minutes at −50° C. The reaction mixture is subsequently stirred for 1 hour at −55° C. and then for 1 hour whilst allowing the temperature to rise gradually to about 20° C. The reaction mixture is subsequently poured into distilled water (1350 cc) and extraction is then carried out twice with ethyl acetate (1250 cc in total). The organic extracts are combined, washed three times with distilled water (3000 cc in total), dried over anhydrous sodium sulphate and concentrated to dryness under reduced pressure (1 mm Hg; 0.13 kPa) at 70° C. The residue (99 g) is dissolved in boiling ethanol (250 cc) and the solution, to which decolourising charcoal (0.5 g) is added, is filtered hot and then kept, after cooling, for 2 hours at a temperature of about 5° C. The crystals which have appeared are filtered off and washed twice with ethanol (30 cc in total). After drying under reduced pressure (20 mm Hg; 2.7 kPa) at a temperature of about 20° C., a product (22.1 g) is obtained and this is dissolved in boiling ethanol (120 cc). The solution, to which decolourising charcoal (0.5 g) is added, is filtered hot and then kept, after cooling, for 2 hours 30 minutes at a temperature of about 5° C. The crystals which have appeared are filtered off and washed twice with ethanol (12 cc in total). After drying under reduced pressure (20 mm Hg; 2.7 kPa) at a temperature of about 20° C., a product (17.7 g) is obtained and this is dissolved in boiling ethanol (83 cc). The solution, to which decolourising charcoal (0.5 g) is added, is filtered hot and then kept, after cooling, for 2 hours 30 minutes at a temperature of about 5° C. The resulting crystals are filtered off and washed twice with ethanol (10 cc in total). After drying under reduced pressure (1 mm Hg; 0.13 kPa) at 60° C., N-ethyl-2-(pyrid-2-yl)tetrahydrothiophene-2-carbothioamide (13.9 g), melting at 96° C., is obtained.

EXAMPLE 17

By following the procedure of Example 16 but using 2-(pyrid-2-yl)tetrahydrothiophene (45 g) and n-butyl isothiocyanate (78 g) as the starting materials, a crude product (120 g) is obtained. The latter is dissolved in 2 N hydrochloric acid (700 cc) and extraction is carried out twice with ethyl acetate (400 cc in total). The aqueous solution is neutralised by adding sodium bicarbonate and extraction is then carried out twice with ethyl acetate (400 cc in total). The organic extracts are combined, washed three times with distilled water (480 cc in total), dried over anhydrous sodium sulphate and concentrated to dryness under reduced pressure (20 mm Hg; 2.7 kPa) at 70° C. The residue (56 g) is chromatographed on neutral silica gel (560 g) contained in a column of diameter 5.2 cm. Elution is carried out successively with cyclohexane (1000 cc), a cyclohexane-ethyl acetate mixture (98:2 by volume; 500 cc), a cyclohexane-ethyl acetate mixture (96:4 by volume; 500 cc), a cyclohexane-ethyl acetate mixture (90:10 by volume; 1000 cc) and a cyclohexane-ethyl acetate mixture (85:15 by volume; 4000 cc), three 1000 cc fractions, two 500 cc fractions and three 1000 cc fractions being collected. Fractions 4 to 6 are combined and concentrated to dryness under reduced pressure (20 mm Hg; 2.7 kPa) at 40° C. The residue (43.4 g) is distilled under reduced pressure (0.8–1.1 mm Hg; 0.11 to 0.14 kPa) and the fraction boiling between 180° C. and 191° C. is isolated. An oil (37.7 g) is thus obtained and this is chromatographed on neutral silica gel (770 g) contained in a column of diameter 5.7 cm. Elution is carried out successively with cyclohexane (16 liters) and a cyclohexane-ethyl acetate mixture (95:5 by volume; 7 liters), twenty-three 1000 cc fractions being collected. Fractions 21 to 23 are combined and concentrated to dryness under reduced pressure (20 mm Hg; 2.7 kPa) at 70° C. The residue (11 g) is distilled under reduced pressure (0.6 mm Hg; 0.08 kPa). N-n-Butyl-2-(pyrid-2-yl)tetrahydrothiophene-2-carbothioamide (7.7 g), boiling between 178° C. and 183° C., is thus obtained.

EXAMPLE 18

A mixture of anhydrous hexamethylphosphorotriamide and anhydrous tetrahydrofuran (47:53 by volume; 145 cc) is added dropwise, in the course of 15 minutes, to a 1.6 M solution of n-butyllithium in hexane (170 cc), which is kept under a nitrogen atmosphere and has been cooled to −60° C. A solution of 2-(4-methylpyrid-2-yl)-tetrahydrothiophene (45.5 g) in a mixture of anhydrous hexamethylphosphorotriamide and anhydrous tetrahydrofuran (47:53 by volume; 145 cc) is then added in the course of 15 minutes. After stirring for 15 minutes at −60° C., a solution of methyl isothiocyanate (20 g) in a mixture of anhydrous hexamethylphosphorotriamide and anhydrous tetrahydrofuran (47:53 by volume; 145 cc) is added in the course of 20 minutes at a temperature of about −60° C. The reaction mixture is subsequently stirred for 1 hour at a temperature of about −65° C. and then for 45 minutes whilst allowing the temperature to rise gradually to +5° C. It is then poured into distilled water (730 cc) and extraction is carried out three times with ethyl acetate (1430 cc in total). The organic extracts are combined, washed three times with distilled water (2250 cc in total), dried over anhydrous sodium sulphate and concentrated to dryness under reduced pressure (20 mm Hg; 2.7 kPa) at 70° C. The residue (40.8 g) is dissolved in boiling ethanol (400 cc) and the solution, to which decolourising charcoal (0.5 g) is added, is filtered hot and then kept, after cooling, for 1 hour 30 minutes at a temperature of about 0° C. The crystals which have appeared are filtered off and washed with ethanol (15 cc) and then twice with diisopropyl ether (60 cc in total).

After drying under reduced pressure (20 mm Hg; 2.7 kPa) at a temperature of about 20° C., a product (14 g) is obtained and this is redissolved in a boiling mixture of ethanol and acetonitrile (94:6 by volume; 480 cc). The solution, to which decolourising charcoal (0.5 g) is added, is filtered hot and then kept, after cooling, for 2 hours at a temperature of about 5° C. The crystals which have appeared are filtered off and washed with ethanol (15 cc) and then twice with diisopropyl ether (30 cc in total). After drying under reduced pressure (1 mm Hg; 0.13 kPa) at a temperature of 60° C., N-methyl-2-(4-methylpyrid-2-yl)tetrahydrothiophene-2-carbothioamide (12.3 g), melting at 181° C., is obtained.

2-(4-Methylpyrid-2-yl)tetrahydrothiophene can be prepared in accordance with the method described in Example 1 for the preparation of 2-(pyrid-2-yl)tetrahydrothiophene. Using (4-methylpyrid-2-yl)methyl 3-chloropropyl sulphide (293 g) and potassium tert.-butylate (234 g) as the starting materials, 2-(4-methylpyrid-2-yl)tetrahydrothiophene (177 g) is obtained in the form of a brown oil [Rf=0.66; chromatography on a thin layer of silica gel; solvent: ethyl acetatecyclohexane (50:50 by volume)].

(4-Methylpyrid-2-yl)methyl 3-chloropropyl sulphide can be prepared in accordance with the method described in Example 1 for the preparation of pyrid-2-ylmethyl 3-chloropropyl sulphide. Using 2-(4-methylpyrid-2-ylmethyl)isothiourea dihydrochloride (411 g) and 1-bromo-3-chloropropane (271 g) as the starting materials, (4-methylpyrid-2-yl)methyl 3-chloropropyl sulphide (293 g) is obtained in the form of a yellow oil [Rf=0.60; chromatography on a thin layer of silica gel; solvent: ethyl acetate-cyclohexane (50:50 by volume)].

2-(4-Methylpyrid-2-ylmethyl)isothiourea dihydrochloride can be prepared in accordance with the method described in Example 1 for the preparation of 2-(pyrid-2-ylmethyl)isothiourea dihydrochloride. Using 2-chloromethyl-4-methylpyridine hydrochloride (376 g) and thiourea (185 g) as the starting materials, 2-(4-methylpyrid-2-ylmethyl)isothiourea dihydrochloride (411 g), melting at 220° C., is obtained.

2-Chloromethyl-4-methylpyridine hydrochloride can be prepared in accordance with the method of W. Mathes and H. Schüly, Angew. Chem. International Edition, 2, 144 (1963).

EXAMPLE 19

By following the procedure of Example 18 but using 2-(5-methylpyrid-2-yl)tetrahydrothiophene (26 g) and methyl isothiocyanate (11.4 g) as the starting materials, a partially crystalline crude product (33 g) is obtained and this is washed twice with diisopropyl ether (300 cc in total). After drying at ordinary pressure at a temperature of about 20° C., a product (19 g) is obtained and this is dissolved in boiling ethanol (120 cc). After filtering hot, the solution is kept for 15 hours at a temperature of about 20° C. and then for 1 hour at a temperature of about 0° C. The crystals which have appeared are filtered off, washed with ethanol (15 cc) and then twice with diisopropyl ether (60 cc in total) and dried under reduced pressure (20 mm Hg; 2.7 kPa) at a temperature of about 20° C. The resulting product (8.4 g) is chromatographed on silica (88 g) contained in a column of diameter 3 cm. Elution is carried out successively with a cyclohexane-ethyl acetate mixture (95:5 by volume; 300 cc), a cyclohexane-ethyl acetate mixture (90:10 by volume; 300 cc), a cyclohexane-ethyl acetate mixture (85:15 by volume; 300 cc), a cyclohexane-ethyl acetate mixture (80:20 by volume; 300 cc) and then a cyclohexane-ethyl acetate mixture (75:25 by volume; 1500 cc), 300 cc fractions being collected. Fractions 5 to 9 are combined and concentrated to dryness under reduced pressure (20 mm Hg; 2.7 kPa) at 40° C. The resulting residue (7.8 g) is dissolved in boiling ethanol (32 cc) and the solution, to which decolourising charcoal (0.1 g) is added, is filtered hot and then kept, after cooling, for 1 hour at a temperature of about 5° C. The crystals which have appeared are filtered off and washed twice with ethanol (4 cc in total). After drying under reduced pressure (1 mm Hg; 0.13 kPa) at 55° C., N-methyl-2-(5-methylpyrid-2-yl)-tetrahydrothiophene-2-carbothioamide (6.2 g), melting at 134° C., is obtained.

2-(5-Methylpyrid-2-yl)tetrahydrothiophene can be prepared in accordance with the method described in Example 1 for the preparation of 2-(pyrid-2-yl)-tetrahydrothiophene. Using (5-methylpyrid-2-yl)methyl 3-chloropropyl sulphide (110.3 g) and potassium tert.-butylate (89 g) as the starting materials, 2-(5-methylpyrid-2-yl)tetrahydrothiophene (74.7 g) is obtained in the form of a brown oil [Rf=0.65; chromatography on a thin layer of silica gel; solvent: ethyl acetate-cyclohexane (50:50 by volume)].

(5-Methylpyrid-2-yl)methyl 3-chloropropyl sulphide can be prepared in accordance with the method described in Example 1 for the preparation of pyrid-2-ylmethyl 3-chloropropyl sulphide. Using 2-(5-methylpyrid-2-ylmethyl)isothiourea dihydrochloride (160 g) and 1-bromo-3-chloropropane (106 g) as the starting materials, (5-methylpyrid-2-yl)methyl 3-chloropropyl sulphide (110.3 g) is obtained in the form of a yellow oil [Rf=0.60; solvent: ethyl acetate-cyclohexane (50:50 by volume)].

2-(5-Methylpyrid-2-ylmethyl)isothiourea dihydrochloride can be prepared in accordance with the method described in Example 1 for the preparation of 2-(pyrid-2-ylmethyl)isothiourea dihydrochloride. Using 2-chloromethyl-5-methylpyridine hydrochloride (170 g) and thiourea (86 g) as the starting materials, 2-(5- methylpyrid-2-ylmethyl)isothiourea dihydrochloride (160 g) is obtained.

2-Chloromethyl-5-methylpyridine hydrochloride can be prepared in accordance with the method described by R. Nicoletti and M. L. Forcellese, Gazz. Chim. Ital., 97, 148 (1967).

EXAMPLE 20

By following the procedure of Example 18 but using 2-(4-n-butylpyrid-2-yl)tetrahydrothiophene (14.4 g) and a 1.6 M solution of n-butyllithium in hexane (65 cc) as the starting materials, a crude product (24 g) is obtained and this is chromatographed on neutral silica gel (250 g) contained in a column of diameter 4 cm. Elution is carried out successively with cyclohexane (600 cc), a cyclohexane-ethyl acetate mixture (97:3 by volume; 1500 cc), a cyclohexane-ethyl acetate mixture (95:5 by volume; 1000 cc), a cyclohexane-ethyl acetate mixture (92:8 by volume; 500 cc) and a cyclohexane-ethyl acetate mixture (90:10 by volume; 8000 cc), one 600 cc fraction and twenty-two 500 cc fractions being collected. Fractions 16 to 23 are combined and concentrated to dryness under reduced pressure (20 mm Hg; 2.7 kPa) at 70° C. The resulting residue (9.7 g) is dissolved in boiling ethanol (45 cc) and the solution, to which decolourising charcoal (0.1 g) is added, is filtered hot and then kept, after cooling, for 1 hour at a temperature of about 0° C. The crystals which have appeared are filtered off, washed with ethanol (5 cc) and dried under reduced pressure (20 mm Hg; 2.7 kPa) at a temperature of about 20° C. The resulting product (6.3 g) is dissolved in boiling ethanol (25 cc) and the solution, to which decolourising charcoal (0.1 g) is added, is filtered hot and then kept, after cooling, for 1 hour at a temperature of about 0° C. The crystals which have appeared are filtered off, washed with ethanol (3 cc) and dried under reduced pressure (20 mm Hg; 2.7 kPa) at a temperature of about 20° C. The resulting product (5.4 g) is dissolved in boiling diisopropyl ether (85 cc) and the solution, to which decolourising charcoal (0.1 g) is added, is filtered hot and then kept, after cooling, for 35 minutes at a temperature of about 5° C. The crystals which have appeared are filtered off, washed twice with diisopropyl ether (24 cc in total) and dried under reduced pressure (1 mm Hg; 0.13 kPa) at 45° C. 2-(4-n-Butylpyrid-2-yl)-2-methylaminocarbothioyl-tetrahydrothiophene (4.2 g), melting at 102° C., is thus obtained.

2-(4-n-Butylpyrid-2-yl)tetrahydrothiophene can be prepared in accordance with the method described in Example 1 for the preparation of 2-(pyrid-2-yl)tetrahydrothiophene. Using (4-n-butylpyrid-2-yl)-methyl 3-chloropropyl sulphide (22.9 g) as the starting material, 2-(4-n-butylpyrid-2-yl)tetrahydrothiophene (14.4 g) is obtained in the form of a brown oil [Rf=0.64; chromatography on a thin layer of silica gel; solvent: ethyl acetate-cyclohexane (50:50 by volume)].

(4-n-Butylpyrid-2-yl)methyl 3-chloropropyl sulphide can be prepared in accordance with the method described in Example 1 for the preparation of pyrid-2-ylmethyl 3-chloropropyl sulphide. Using 2-(4-n-butylpyrid-2-ylmethyl)isothiourea dihydrochloride (28.3 g) and 1-bromo-3-chloropropane (16.1 g) as the starting materials, (4-n-butylpyrid-2-yl)methyl 3-chloropropyl sulphide (22.9 g) is obtained in the form of a yellow liquid [Rf=0.60; chromatography on a thin layer of silica gel; solvent: ethyl acetate-cyclohexane (50:50 by volume)].

2-(4-n-Butylpyrid-2-ylmethyl)isothiourea dihydrochloride can be prepared in accordance with the method described in Example 1 for the preparation of 2-(pyrid-2-ylmethyl)isothiourea dihydrochloride. Using 4-n-butyl-2-chloromethylpyridine hydrochloride (26.9 g) and thiourea (11.3 g) as the starting materials, 2-(4-n-butylpyrid-2-ylmethyl)isothiourea dihydrochloride (26.4 g), melting at 209° C., is obtained.

4-n-Butyl-2-chloromethylpyridine hydrochloride can be prepared in the following manner:

4-n-Butyl-2-hydroxymethylpyridine (28.9 g) is added dropwise, in the course of 12 minutes, to thionyl chloride (64 g) whilst allowing the temperature to rise gradually to 65° C. The reaction mixture is subsequently stirred for 4 hours under reflux and is then concentrated to dryness under reduced pressure (20 mm Hg; 2.7 kPa) at 75° C. The resulting residue (45 g) is cautiously taken up in distilled water (350 cc) and extraction is carried out twice with diethyl ether (250 cc in total). The aqueous solution is rendered alkaline with 2 N sodium hydroxide solution (135 cc) and extraction is carried out with diethyl ether (200 cc). The ether solution is dried over anhydrous sodium sulphate and filtered, a 3 N solution of hydrogen chloride in ethanol (100 cc) is added and the mixture is concentrated to dryness under reduced pressure (20 mm Hg; 2.7 kPa) at 70° C. 4-n-Butyl-2-chloromethylpyridine hydrochloride (26.9 g), melting at 95° C., is thus obtained.

4-n-Butyl-2-hydroxymethylpyridine can be prepared in accordance with the method of F. Arena et al., Il Farmaco Ed. Sc., 33(5), 324 (1978).

The present invention includes within its scope pharmaceutical compositions which comprise, as active ingredient, at least one of the compounds of general formula I, or—when appropriate—a non-toxic pharmaceutically acceptable salt thereof, in association with a compatible pharmaceutically acceptable carrier, adjuvant, or physiologically active product. The invention includes especially such preparations made up for oral, parenteral or rectal administration.

Solid compositions for oral administration include tablets, pills, powder and granules. In such solid compositions the active compound is admixed with at least one inert diluent such as sucrose, lactose or starch. The compositions may also comprise, as is normal practice, additional substances other than inert diluents e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules or absorbable material (preferably gelatin) containing the active substance with or without the addition of diluents or excipients, e.g. in the form of a powder.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

In human therapy, the 2-(pyrid-2-yl)-tetrahydrothiophene derivatives of the present invention are particularly useful in the treatment of gastro-intestinal ulcers. The doses depend on the desired effect and the duration of the treatment; for an adult, they are generally between 50 and 1000 mg per day, administered orally in one or more doses.

In general, the physician will determine the posology considered appropriate, taking into account the age, weight and all the other factors intrinsic to the patient to be treated.

The following Example illustrates pharmaceutical compositions according to the invention.

EXAMPLE 21

Tablets containing 50 mg doses of active compound and having the following composition are prepared in accordance with the usual technique:
N-methyl-2-(pyrid-2-yl)tetrahydrothiophene-2-carbothioamide: 50 mg
starch: 15 mg
colloidal silica: 9.5 mg
magnesium stearate: 0.5 mg

We claim:

1. A 2-(pyrid-2-yl)tetrahydrothiophene compound of the formula:

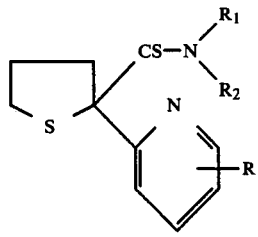

wherein R represents hydrogen or alkyl of 1 through 4 carbon atoms, and $R_1$ and $R_2$ represent hydrogen or alkyl of 1 through 15 carbon atoms, or alkyl of 1 through 15 carbon atoms substituted by one substituent selected from (i) hydroxy, (ii) alkylamino in which the alkyl radical is of 1 through 4 carbon atoms, (iii) dialkylamino in which the alkyl radicals are of 1 through 4 carbon atoms, (iv) phenyl, (v) carboxy, and (vi) alkoxycarbonyl in which the alkoxy radical is of 1 through 4 carbon atoms, or $R_1$ and $R_2$ together with the nitrogen atom to which they are attached represent piperidino, morpholino, or piperazin-1-yl which may be substituted on the 4-position nitrogen atom by alkyl of 1 to 4 carbon atoms, and pharmaceutically acceptable acid addition salts thereof or pharmaceutically acceptable metal salts or salts with pharmaceutically acceptable nitrogen-containing bases.

2. A compound according to claim 1 wherein R is as defined in claim 1, $R_1$ represents hydrogen or alkyl of 1 through 4 carbon atoms, and $R_2$ represents hydrogen.

3. A compound according to claim 1 wherein R is as defined in claim 1, $R_1$ represents alkyl of 1 through 4 carbon atoms and $R_2$ represents hydrogen.

4. A compound according to claim 1 wherein R is as defined in claim 1, $R_1$ represents hydrogen or methyl, and $R_2$ represents hydrogen.

5. A compound according to claim 1 which is N-methyl-2-(pyrid-2-yl)tetrahydrothiophene-2-carbothioamide.

6. A compound according to claim 1 which is N-methyl-2-(6-methypyrid-2-yl)tetrahydrothiophene-2-carbothioamide.

7. A compound according to claim 1 which is N-methyl-2-(5-methylpyrid-2-yl)tetrahydrothiophene-2-carbothioamide.

8. A compound according to claim 1 which is N-methyl-2-(4-methylpyrid-2-yl)tetrahydrothiophene-2-carbothioamide.

9. A compound according to claim 1 which is 2-(pyrid-2-yl)tetrahydrothiophene-2-carbothioamide.

10. A pharmaceutical composition which comprises an effective amount of a 2-(pyrid-2-yl)tetrahydrothiophene compound or a pharmaceutically acceptable salt thereof as claimed in claim 1, in association with at least one compatible pharmaceutically acceptable carrier or adjuvant.

11. A pharmaceutical composition according to claim 10 which contains an effective amount of a said compound or pharmaceutically acceptable salt thereof, for the treatment of gastro-intestinal ulcers, and is in a form suitable for oral administration.

* * * * *